(12) United States Patent
Green et al.

(10) Patent No.: US 7,365,139 B2
(45) Date of Patent: Apr. 29, 2008

(54) POLYMERISATION CATALYST

(75) Inventors: Simon Michael Green, Egham (GB); Peter James Maddox, Staines (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 11/633,561

(22) Filed: Dec. 5, 2006

(65) Prior Publication Data

US 2007/0161761 A1 Jul. 12, 2007

Related U.S. Application Data

(62) Division of application No. 10/477,734, filed as application No. PCT/GB02/02247 on May 14, 2002, now Pat. No. 7,163,990.

(30) Foreign Application Priority Data

May 17, 2001 (GB) ................................ 0112023.7

(51) Int. Cl.
C08F 4/42 (2006.01)

(52) U.S. Cl. .................... 526/161; 526/348; 526/317.1; 502/103; 502/152

(58) Field of Classification Search ................ 526/161, 526/348, 317.1; 502/103, 152
See application file for complete search history.

(56) References Cited

FOREIGN PATENT DOCUMENTS

| WO | WO 99/12981 | 1/1999 |
|---|---|---|
| WO | WO 00/50470 | 8/2000 |
| WO | WO 01/14391 | 3/2001 |

OTHER PUBLICATIONS van Meurs et al., J.Am.Chem.Soc., 127, 9913-9923 (2005).*
Dash, B. et al., "Cobalt (II), nickel (II), copper (II), and zinc (II) complexes of Schiff base derived from 4-aryl-2-aminothiazoles and salicyaldehyde", Chemical Abstracts, vol. 83, No. 4, Jul. 28, 1975.
Pancholi et al., "Ni(II), Cu (II), and Co (II) complexes of Schiff base derived from 2-amino-5methyl-4-phenylthiazole", Chemical Abstracts, vol. 121, No. 10, Sep. 5, 1994.
Garnovskii, et al., "Competitive coordination in the N-, O-, S-donating ligand sequence: cobalt (II), nickel (II), copper (II), and palladium (II) chelate complexes with o-N-tosylamino (oxy,mercapto)-R-arylidene-4-aminoantipyrine", Chemical Abstracts, vol. 123, No. 12, Sep. 18, 1995.
Pancholi et al., Manganese (II) complexes of Schiff base derived from substituted 2-amonothiazoles, Chemical Abstracts, vol. 125, No. Sep. 2, 1996.
Mahapatra, B. et al., "Complexes of divalent cobalt ,nickel, copper, iron, manganese, cadmim and mercury with tridentate ONN donor Schiff bases", Chemical Abstracts, vol. 112, No. 14, Apr. 2, 1990.
Spinu, Cezar et al., "Studies on N-'2-thienylmethylidene!-2-aminothiazole complexes of Fe (II), Co (II), Ni (II), Cu (II), Zn (II) and Cd (II)", Chemical Abstracts, vol. 135.
Sharma, R.C. et al., "Synthesis and structural studies of Co (II), Ni (II), Zn (II), and Cd(II) metal complexes of 2-hydroxy-5-methylbenzene-1, 3-bis (methylen e-2-aminothiazole)", Chemical Abstracts, vol. 136.
Meurs et al., J. Am. Chem. Soc. 127, 9913-9923 (2005).

* cited by examiner

*Primary Examiner*—Ling-Sui Choi
(74) *Attorney, Agent, or Firm*—Finnegan, Henderson, Farabow, Garrett and Dunner, L.L.P.

(57) ABSTRACT

A complex of transition metal Ti, Fe, Co, Ni, Cr, Mn, Ta, Rh, Y, Sc, Ru, Pd, Zr, Hf, V or Nb and a mono-, bi-, tri-, or tetra-dentate ligand, wherein at least one of the donor atoms of the ligand is a nitrogen atom N with a 5-membered heterocyclic substituent joined to the N by a carbon atom. The complex is preferably Formula (I) wherein $R^5$—N-G-$X^1$ is a bi-, tri, or tetra-dentate ligand, N is joined to G by an imine linkage; G is a bridging group which can contain a third or fourth donor atom; $X^1$ is —O or —S if the $X^1$-M bond is covalent, or if the $X^1$-M bond is dative $X^1$ is =S, —$PR^7R^8$, —$PR^8R^9$, =$NR^7$, =$NR^8$, —$NR^7R^8$ or —$NR^8R^9$; $R^5$ and $R^7$ are 5-membered heterocyclic substituents joined to the nitrogen (or phosphorus) atoms via a carbon atom: $R^8$ and $R^9$ are hydrocarbyl or heterohydrocarbyl, substituted hydrocarbyl or aryl substituent; X represents an atom or group covalently or ionically bonded to the transition metal M: L is a group datively bound to M, and n is from 0 to 5; q is 1 or 2. The complexes find use as polymerisation catalysts, preferably with an activator, e.g. MAO (I)

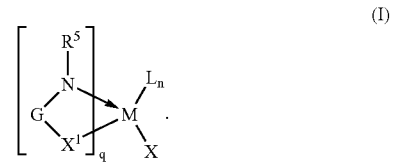

28 Claims, No Drawings

POLYMERISATION CATALYST

RELATED APPLICATIONS

This application is a divisional of U.S. application Ser. No. 10/477,734 filed Nov. 14, 2003 now U.S. Pat. No. 7,163,990, which is a §371 of International Application No. PCT/GB02/02247 filed May 14, 2002 which claims priority of Great Britain Application No. 0112023.7 filed May 17, 2001.

The present invention relates to transition metal complex compounds, to polymerisation catalysts based thereon and to their use in the polymerisation and copolymerisation of olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10-50 bar) and low temperature (for example 50 to 150° C.).

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

An object of the present invention is to provide a novel catalyst suitable for polymerising and oligomerising monomers, for example, olefins such as α-olefins containing from 2 to 20 carbon atoms, and especially for polymerising ethylene alone, propylene alone, or for copolymerising ethylene or propylene with other 1-olefins such as $C_{2-20}$ α-olefins.

WO 99/12981 discloses that ethylene and other 1-olefins may be polymerised by contacting it with certain late transition metal complexes of selected 2,6-pyridinecarboxaldehydebis (imines) and 2,6-diacylpyridinebis (imines).

WO 00/50470 discloses in its broadest aspect a polymerisation catalyst comprising a transition metal complex in which at least one of the donor atoms of the ligand is a nitrogen atom substituted by a 1-pyrrolyl or substituted 1-pyrrolyl group. Specific examples include ligands such as the following, where the R groups are typically alkyl groups:

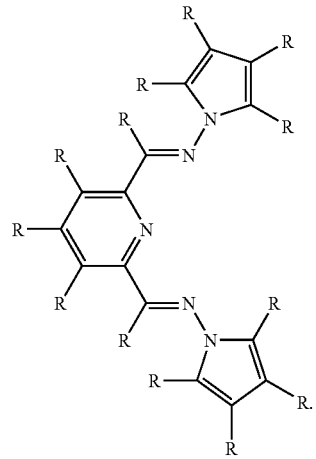

WO01/14391 discloses similar bisiminidato metal complexes in which two of the donor atoms of the ligand are nitrogen atoms linked to further nitrogen atoms of a substituent which may be a five-membered heterocyclic substituent.

The chemistry of C—N bonds is well-known to be significantly different to that of N—N bonds, including the type exemplified by N-iminopyrrole examples in the prior art. In particular, ligands containing N-donor atoms linked to a C atom would be expected to contribute a different amount of electronic charge to the metal centre compared with an N donor linked to another N atom, and this is likely to have a significant effect on the overall catalytic properties of the complex.

We have discovered a further class of complexes that are effective polymerisation catalysts in which at least one, preferably two of the donor atoms of the ligand is a nitrogen atom joined to a carbon atom of a five-membered heterocyclic substituent.

Accordingly in its broadest aspect, the present invention provides a metal complex being Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV] or Nb[V], ligated by a monodentate, bidentate, tridentate or tetradentate ligand, wherein at least one of the donor atoms of the ligand is a nitrogen atom substituted by a five-membered heterocyclic substituent joined to the nitrogen atom by a carbon atom.

Preferably the complex is of the Formula (I)

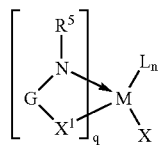

Formula (I)

wherein the structure $R^5$—N-G-$X^1$ represents a bidentate, tridentate or tetradentate ligand, in which N is a nitrogen joined to G by an imine linkage; G is a bridging group which optionally contains a third or fourth donor atom; $X^1$ is —O or —S if the $X^1$-M bond is covalent, or if the $X^1$-M bond is dative, $X^1$ is =S, —$PR^7R^8$, —$PR^8R^9$, =$NR^7$, =$NR^8$, —$NR^7R^8$ or —$NR^8R^9$; $R^5$ is a five-membered heterocyclic substituent joined to the nitrogen atom via a carbon atom; $R^7$ is a five-membered heterocyclic substituent joined to the nitrogen or phosphorus atom via a carbon atom; and $R^8$ and $R^9$ are hydrocarbyl or heterohydrocarbyl, substituted hydrocarbyl or aryl substituent; M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV], Nb[V]; X represents an atom or group covalently or ionically bonded to the transition metal M; and L is a group datively bound to M, and n is from 0 to 5; q is 1 or 2.

Preferably $X^1$ is =$NR^7$. In the case where q is 2, the two ligands may be joined to form a single tetradentate ligand. However preferably q is 1, and the ligand is bidentate or tridentate.

Preferably $R^5$ and $R^7$ each independently have the structure

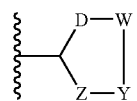

wherein D, W, Y and Z are each independently selected from CR, CRR', N, NR O, S, PR or PRR' where R and R' are each independently H, $C_1$-$C_{10}$ alkyl, $C_1$-$C_{10}$ heteroalkyl or $C_6$-$C_{20}$ aryl or aralkyl, with the proviso that at least one of D, W, Y and Z is not CR or CRR'. It is preferred that the ring is heteroaromatic, with two of D, W, Y and Z being CR, and the other two being independently selected from N, NR, O or S.

Preferably one or both of the $R^5$ and $R^7$ rings are substituted at one or both positions adjacent the linkage to the nitrogen atom. Such substituents are preferably methyl, ethyl, isopropyl or phenyl optionally substituted with $C_1$-$C_4$ alkyl. A preferred structure for $R^5$ and $R^7$ is the following:

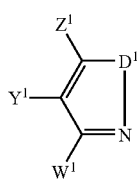

where D' is NR, O or S where R is H, $C_1$-$C_6$ alkyl or $C_6$-$C_{20}$ aryl or aralklyl, and two of $W^1$, $Y^1$ and $Z^1$ are independently H, $C_1$-$C_6$ aryl or $C_6$-$C_{20}$ aryl or aralkyl, whilst the third is replaced by a direct bond to the nitrogen atom to which $R^5$ or $R^7$ is attached. Preferably $Y^1$ is replaced by the bond to the nitrogen atom. Preferably $W^1$ and $Z^1$ are $C_1$-$C_6$ alkyl or $C_6$-$C_{20}$ aryl or aralkyl. Preferably $D^1$ is NR.

A particularly preferred substituent for both $R^5$ and $R^7$ is the substituent having the formula (II):

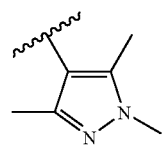

Formula (II)

Generally, the above five-membered heterocyclic substituent may replace a pyrrolyl or substituted pyrrolyl substituent attached to a donor nitrogen atom in any of the complexes disclosed in WO 00/50470.

A second aspect of the invention comprises a complex represented by the general formula (III)

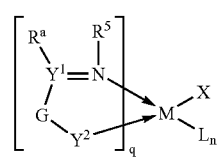

Formula (III)

wherein M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV], Nb[V]; X represents an atom or group covalently or ionically bonded to the transition metal M; $Y^1$ is C or P($R^c$); $Y^2$ is —O($R^7$), —O (in which case the bond from O to M is covalent), —C($R^b$)=O, —C($R^b$)=N($R^7$), —P($R^b$)($R^d$)=N($R^7$) or —P($R^b$)($R^d$)=O; $R^5$ and $R^7$ are each independently five-membered heterocyclic substituents joined to the nitrogen atom via a carbon atom; $R^a$, $R^b$, $R^c$, $R^d$ are each independently selected from hydrogen, halogen, hydrocarbyl, substituted hydrocarbyl, heterohydrocarbyl, substituted heterohydrocarbyl or SiR'$_3$ where each R' is independently selected from hydrogen, halogen, hydrocarbyl, substituted hydrocarbyl, heterohydrocarbyl and substituted heterohydrocarbyl, and any adjacent ones may be joined together to form a ring; G is either a direct bond between $Y^1$ and $Y^2$, or is a bridging group which optionally contains a third atom linked to M when q is 1; L is a group datively bound to M; n is from 0 to 5; and q is 1 or 2.

Preferably the above complex has the formula (IV)

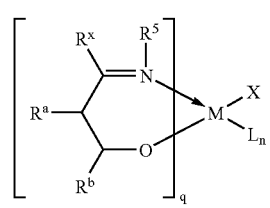

Formula (IV)

wherein M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV], Nb[V]; X represents an atom or group covalently or ionically bonded to the transition metal M; $R^a$, $R^b$ and $R^x$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; $R^5$ is a five-membered heterocyclic substituent joined to the nitrogen atom via a carbon atom; and L is a group datively bound to M; n is from 0 to 5; and q is 1 or 2.

Preferably M is a Group IV metal, particularly Ti, Zr, Cr, Ni or Pd. Preferably $R^a$ and $R^b$ are joined together to form a phenyl, which is preferably substituted. Preferred substituents are $C_1$-$C_6$ alkyl or $C_6$-$C_{24}$ aryl or aralkyl. In particular, the phenyl group may be substituted at the position adjacent the oxygen linkage with a t-butyl group or an anthracenyl group, which may itself be substituted.

An alternative preferred complex of the invention has the Formula (V)

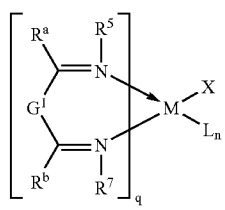

Formula (V)

wherein $R^5$ and $R^7$ are each independently five-membered heterocyclic substituents joined to the nitrogen atom via a carbon atom; $R^a$, and $R^b$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], V[III], V[IV], Nb[II], Nb[III], Nb[IV], Nb[V]; X represents an atom or group covalently or ionically bonded to the transition metal M; L is a group datively bound to M; n is from 0 to 5; and q is 1 or 2; and $G^1$ is either a direct bond between the two C=N groups, or is a bridging group which optionally contains a third donor atom when q is 1.

An example of the above is the complex of Formula (VI):

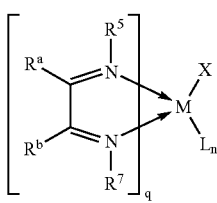

Formula (VI)

wherein M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV], Nb[V]; X represents an atom or group covalently or ionically bonded to the transition metal M; $R^a$ and $R^b$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; wherein $R^5$ and $R^7$ are each independently five-membered heterocyclic substituents joined to the nitrogen atom via a carbon atom; and L is a group datively bound to M; n is from 0 to 5; and q is 1 or 2.

Preferably M is Ni or Pd.

A particularly preferred complex has the following Formula (VII)

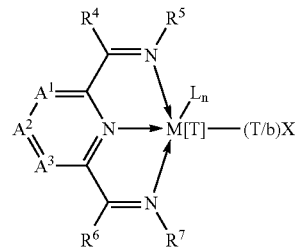

Formula (VII)

wherein M[T] is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV], Nb[V]; X represents an atom or group covalently or ionically bonded to the transition metal M; T is the oxidation state of the transition metal M and b is the valency of the atom or group X; $A^1$ to $A^3$ are each independently N or P or CR, with the proviso that at least one is CR; R, $R^4$ and $R^6$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl; and $R^5$ and $R^7$ are each independently five-membered heterocyclic substituents joined to the nitrogen atom via a carbon atom.

Preferably $A^1$ to $A^3$ are each independently CR where each R is as defined above. In alternative preferred embodiments, $A^1$ and $A^3$ are both N and $A^2$ is CR, or one of $A^1$ to $A^3$ is N and the others are independently CR.

The metal M is preferably Fe(II), Fe(III) or Co(II).

Each of the nitrogen atoms is coordinated to the metal M by a "dative" bond, i.e. a bond formed by donation of a lone pair of electrons from the nitrogen atom. The remaining bonds on each nitrogen atom are covalent bonds formed by electron sharing between the nitrogen atoms and the organic ligand as shown in the defined formula for the transition metal complex illustrated above.

The atom or group represented by X in the above complexes can be, for example, selected from halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl, or β-diketonates. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate. Preferred examples of the atom or group X are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

L may be for example an ether such as tetrahydrofuran or diethylether, an alcohol such as ethanol or butanol, a primary, secondary or tertiary amine, or a phosphine.

The complexes of the present invention may be used as catalysts for the polymerisation of 1-olefins, optionally in conjunction with an activator compound. For example the catalysts can be used for the polymerisation of 1-olefins, or the copolymerisation of one or more 1-olefins optionally with other unsaturated monomer. The term "polymerisation" as used throughout this specification is intended to include homopolymerisation, copolymerisation and oligomerisation.

The activator compound for all the catalysts of the present invention is suitably selected from organoaluminium compounds and hydrocarbylboron compounds. Suitable organoaluminium compounds include compounds of the formula $AlR_3$, where each R is independently $C_1$-$C_{12}$ alkyl or halo. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula $[R_6AlO]_s$ and the linear alumoxanes by the formula $R_{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups. Alkylalumoxanes such as methylalumoxane (MAO) are preferred.

Mixtures of alkylalumoxanes and trialkylaluminium compounds are particularly preferred, such as MAO with TMA or TIBA. In this context it should be noted that the term "alkylalumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trimethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula $AlR_3$ additional to any $AlR_3$ compound incorporated within the alkylalumoxane when present.

Examples of suitable hydrocarbylboron compounds are boroxines, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl) phenyl]borate, $H^+(OEt_2)[(bis-3,5-trifluoromethyl)phenyl]$ borate, trityltetra(pentafluorophenyl)borate and tris (pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of metal M in the compound of Formula (I).

An alternative class of activators comprise salts of a cationic oxidising agent and a non-coordinating compatible anion. Examples of cationic oxidising agents include: ferrocenium, hydrocarbyl-substituted ferrocenium, $Ag^+$, or $Pb^{2+}$. Examples of non-coordinating compatible anions are $BF_4^-$, $SbF_6^-$, $PF_6^-$, tetrakis(phenyl)borate and tetrakis(pentafluorophenyl)borate.

A further aspect of the present invention provides a polymerisation catalyst system comprising (1) a complex as hereinbefore defined, (2) an activating quantity of at least one activator compound as defined above, and (3) a neutral Lewis base.

Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitrites, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1): component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures e.g. up to 120° C. can be carried out if desired, e.g. to achieve better mixing of the components. It is preferred to carry out the bringing together of components (1), (2) and (3) in an inert atmosphere (e.g. dry nitrogen) or in vacuo. If it is desired to use the catalyst on a support material (see below), this can be achieved, for example, by performing the catalyst system comprising components (1), (2) and (3) and impregnating the support material preferably with a solution thereof, or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and aminostyrene (ie vinylaniline).

The catalysts of the present invention can if desired comprise more than one of the defined compounds. Alternatively, the catalysts of the present invention can also include one or more other types of transition metal compounds or catalysts, for example, nitrogen containing catalysts such as those described in our copending applications WO 99/12981 or GB 9903402.7. Examples of such other catalysts include 2,6-diacetylpyridinebis (2,4,6-trimethyl anil)$FeCl_2$.

The catalysts of the present invention can also include one or more other types of catalyst, such as those of the type used in conventional Ziegler-Natta catalyst systems, metallocene-based catalysts, monocyclopentadienyl- or constrained geometry based catalysts, or heat activated supported chromium oxide catalysts (e.g. Phillips-type catalyst).

The catalysts of the present invention can be unsupported or supported on a support material, for example, silica, alumina, $MgCl_2$ or zirconia, or on a polymer or prepolymer, for example polyethylene, polypropylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins, comprising contacting the monomeric olefin under polymerisation conditions with the polymerisation catalyst or catalyst system of the present invention. A preferred process comprises the steps of:

a) preparing a prepolymer-based catalyst by contacting one or more 1-olefins with a catalyst system, and b) contacting the prepolymer-based catalyst with one or more 1-olefins, wherein the catalyst system is as defined above.

The present invention also encompasses as another aspect the use of a complex as defined above as a catalyst for the polymerisation of 1-olefins.

In the text hereinbelow, the term "catalyst" is intended to include "catalyst system" as defined previously and also "prepolymer-based catalyst" as defined above.

The catalysts of the invention may be preformed, or may be formed in-situ by adding the components, including the activator, to the polymerisation reactor.

The polymerisation conditions can be, for example, solution phase, slurry phase, gas phase or bulk phase, with polymerisation temperatures ranging from —100° C. to +300° C., and at pressures of atmospheric and above, particularly from 140 to 4100 kPa. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Suitable monomers for use in the polymerisation process of the present invention are, for example, ethylene and $C_{2-20}$ α-olefins, specifically propylene, 1-butene, 1-pentene, 1-hexene, 4-methylpentene-1,1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene. Other monomers include methyl methacrylate, methyl acrylate, butyl acrylate, acrylonitrile, vinyl acetate, and styrene. Preferred monomers for homopolymerisation processes are ethylene and propylene.

The catalysts and process of the invention can also be used for copolymerising ethylene or propylene with each other or with other 1-olefins such as 1-butene, 1-hexene, 4-methylpentene-1, and octene, or with other monomeric materials, for example, methyl methacrylate, methyl acrylate, butyl acrylate, acrylonitrile, vinyl acetate, and styrene.

Irrespective of the polymerisation or copolymerisation technique employed, polymerisation or copolymerisation is typically carried out under conditions that substantially exclude oxygen, water, and other materials that act as catalyst poisons. Also, polymerisation or copolymerisation can be carried out in the presence of additives to control polymer or copolymer molecular weights.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase, bulk phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of transition metal complex in the produced polymer can be very small.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In the slurry phase process and the gas phase process, the catalyst is generally metered and transferred into the polymerisation zone in the form of a particulate solid either as a dry powder (e.g. with an inert gas) or as a slurry. This solid can be, for example, a solid catalyst system formed from the one or more of complexes of the invention and an activator with or without other types of catalysts, or can be the solid catalyst alone with or without other types of catalysts. In the latter situation, the activator can be fed to the polymerisation zone, for example as a solution, separately from or together with the solid catalyst. Preferably the catalyst system or the transition metal complex component of the catalyst system employed in the slurry polymerisation and gas phase polymerisation is supported on one or more support materials. Most preferably the catalyst system is supported on the support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques. Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to the polymerisation zone.

In the slurry phase polymerisation process the solid particles of catalyst, or supported catalyst, are fed to a polymerisation zone either as dry powder or as a slurry in the polymerisation diluent. The polymerisation diluent is compatible with the polymer(s) and catalyst(s), and may be an alkane such as hexane, heptane, isobutane, or a mixture of hydrocarbons or paraffins. Preferably the particles are fed to a polymerisation zone as a suspension in the polymerisation diluent. The polymerisation zone can be, for example, an autoclave or similar reaction vessel, or a continuous loop reactor, e.g. of the type well-known in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

For typical production of impact copolymers, homopolymer formed from the first monomer in a first reactor is reacted with the second monomer in a second reactor. For manufacture of propylene/ethylene impact copolymer in a gas-phase process, propylene is polymerized in a first reactor; reactive polymer transferred to a second reactor in which ethylene or other comonomer is added. The result is an intimate mixture of a isotactic polypropylene chains with chains of a random propylene/ethylene copolymer. A random copolymer typically is produced in a single reactor in which a minor amount of a comonomer (typically ethylene) is added to polymerizing chains of propylene.

Methods for operating gas phase fluidised bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst deactivators a manner known to persons of skill in the art.

Homopolymerisation of ethylene with the catalysts of the invention may produce so-called "high density" grades of polyethylene. These polymers have relatively high stiffness and are useful for making articles where inherent rigidity is required. Copolymerisation of ethylene with higher 1-olefins (e.g. butene, hexene or octene) can provide a wide variety of copolymers differing in density and in other important physical properties. Particularly important copolymers made by copolymerising ethylene with higher 1-olefins with the catalysts of the invention are the copolymers having a density in the range of 0.91 to 0.93. These copolymers which are generally referred to in the art as linear low density polyethylene, are in many respects similar to the so called low density polyethylene produced by the high pressure free radical catalysed polymerisation of ethylene. Such polymers and copolymers are used extensively in the manufacture of flexible blown film.

Propylene polymers produced by the process of the invention include propylene homopolymer and copolymers of propylene with less than 50 mole % ethylene or other alpha-olefin such as butene-1, pentene-1,4-methylpentene-1, or hexene-1, or mixtures thereof. Propylene polymers also may include copolymers of propylene with minor amounts of a copolymerizable monomer. Typically, most useful are normally-solid polymers of propylene containing polypropylene crystallinity, random copolymers of propylene with up to about 10 wt. % ethylene, and impact copolymers containing up to about 20 wt. % ethylene or other alpha-olefin. Polypropylene homopolymers may contain a small amount (typically below 2 wt. %) of other monomers to the extent the properties of the homopolymer are not affected significantly.

Propylene polymers may be produced which are normally solid, predominantly isotactic, poly α-olefins. Levels of stereorandom by-products are sufficiently low so that useful products can be obtained without separation thereof. Typically, useful propylene homopolymers show polypropylene crystallinity and have isotactic indices above 90 and many times above 95. Copolymers typically will have lower isotactic indices, typically above 80-85.

Depending upon polymerisation conditions known in the art, propylene polymers with melt flow rates from below 1 to above 1000 may be produced in a reactor. For many applications, polypropylenes with a MFR from 2 to 100 are typical. Some uses such as for spunbonding may use a polymer with an MFR of 500 to 2000.

Peroxide compounds may be added to ethylene or propylene polymers. For ethylene based polymers, peroxides can be used to give cross-linking in the polymer. For the preparation of high MFR propylene polymers, peroxide compounds may be added during extrusion for controlled rheology to increase the melt flow rate of polymer. Peroxide acts to break long polymer chains and has the effect of both increasing MFR and narrowing the molecular weight distribution (Mw/Mn) or polydispersity. A typical reactor polypropylene powder with an MFR of 2 g/10 min. by controlled rheology treatment with peroxide in an extruder may form a polymer with an MFR of 20-40. By varying the type, amount of, and process conditions using, peroxide, the final polymer MFR may be controlled as known in the art.

Depending upon the use of the polymer product, minor amounts of additives are typically incorporated into the polymer formulation such as acid scavengers, antioxidants, stabilizers, and the like. Generally, these additives are incorporated at levels of about 25 to 2000 ppm, typically from about 50 to about 1000 ppm, and more typically 400 to 1000 ppm, based on the polymer.

In use, polymers or copolymers made according to the invention in the form of a powder are conventionally compounded into pellets. Examples of uses for polymer compositions made according to the invention include use to form fibres, extruded films, tapes, spunbonded webs, moulded or thermoformed products, and the like. The polymers may be blown into films, or may be used for making a variety of moulded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuranone stabilizers, and the like. Various olefin polymer additives are described in U.S. Pat. Nos. 4,318,845, 4,325,863, 4,590,231, 4,668,721, 4,876,300, 5,175,312, 5,276,076, 5,326,802, 5,344,860, 5,596,033, and 5,625,090.

Fillers such as silica, glass fibers, talc, and the like, nucleating agents, and colourants also may be added to the polymer compositions as known by the art.

The present invention is illustrated in the following Examples.

EXAMPLES

Example 1

Preparation of "Ligand 1", 2,6-di-[(1,3,5-trimethyl-4-pyrazolyl)ethanimidoyl]pyridine Acetic acid (glacial, catalytic amount) was added to a solution of diacetylpyridine (1 mmol, 1 eq.) and 4-amino-1,3,5-trimethylpyrazole (4 mmol, 4 eq.) in ethanol (10 mL, absolute). The mixture was refluxed under nitrogen for 16 hours in a test tube containing a suspended Soxhlet thimble filled with activated molecular sieves (3A). After this time the mixture was concentrated under reduced pressure to give the crude product as an orange oily solid. Trituration with petroleum ether furnished a sandy-coloured solid which was subsequently characterised to be the desired compound by IR and $^1$H NMR spectroscopy.

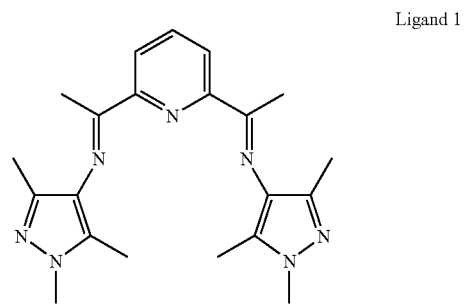

Ligand 1

Example 2

Polymerisation of Ethylene Using an Equimolar Mixture of Ligand 1 and FeCl$_2$

In a glovebox, Ligand 1 (0.05 mmol, 18.9 mg) was mixed with FeCl$_2$ (0.05 mmol) and THF (2.0 mL) was added. The mixture was stirred at room temperature for 1 h before the solvent was removed under vacuum to provide a green powder.

To the powder was added toluene (6.25 mL) to form a fine suspension. From the stirred suspension a 0.5 mL aliquot (0.004 mmol) was transferred to a Schlenk tube and a solution of 10% MAO in toluene was added (0.5 mL, 0.75 mmol). The resulting pink solution was diluted with 20 mL toluene and the Schlenk tube was weighed before being evacuated and refilled with ethylene. The solution was stirred, open to an ethylene supply regulated to 1 bar pressure, for a duration of 1 hour. After this time, the flask was re-weighed before quenching with acidified methanol. A weight-gain of 4.49 g was noted, corresponding to an activity of 1123 g/mmol.h.bar.

The white solid polymer product was isolated by filtration and dried overnight at 40° C. under vacuum before submitting for NMR and GPC analysis. From the filtration washings the organic layer was isolated, and dried over MgSO$_4$ before removing the volatiles in vacuo. The resulting oil was submitted for analysis by GC-MS. GPC analysis of solid product: Mn=500, Mw=1500, PD=2.8. $^{13}$C NMR analysis of solid product (/1000C): saturated ends, 19.8; vinyl ends, 17.4; ethyl branches 1.9; butyl (and longer) branches 0.7; internal olefin 0.8 GC-MS analysis of oil (olefin, rel. area): C6, 2.55%; C8, 8.07%; C10, 11.10%; C12, 13.16%; C14, 13.55%; C16, 13.04%; C18, 11.63%; C20, 9.26%; C22, 6.79%; C24, 4.92%; C26, 2.27%; C28, 0.49%; C30, not measurable.

Example 3

Ethylene/1-hexene Copolymerisation

The polymerisation was carried out exactly as described in Example 2, except that the initially formed catalyst solution (0.5 mL of toluene solution containing 0.004 mmol of Ligand 1+0.5 mL of 10% MAO in toluene) was diluted with 18.6 mL toluene and 0.4 mL 1-hexene (2% v/v 1-hexene). The resulting solution was stirred, open to an ethylene supply regulated to 1 bar pressure, for a duration of 1 hour. After this time, a weight-gain of 4.79 g was noted, corresponding to an activity of 1198 g/mmol.h.bar. The reaction was quenched by addition of acidified methanol, and the white solid polymer product was isolated by filtration and dried overnight at 40° C. GPC analysis showed Mn=500, Mw=1500, Mw/Mn=2.9, Mpk=500. $^{13}$C No analysis of solid product (/1000C): ethyl branches 2.2; butyl branches 1.4; internal olefin 2.0

Example 4

Preparation of 13% MAO on Silica

Toluene (200 mL) was added to a vessel containing silica (ES70X grade, calcined at 200° C. overnight, 20.5 g after calcination) under an inert atmosphere. The slurry was mechanically stirred and MAO (1.5M, 62.1 mmol, 41.4 mL) was added via syringe. The mixture was stirred for 1 hour at 80° C. before removing excess toluene and drying under vacuum to obtain 13% w/w MAO on silica in quantitative yield.

Example 5

Preparation of a Supported Catalyst

Into an vial was weighed 13% MAO on silica (100 mg, prepared according to Example 4). To the vial was then added toluene (2 mL) to form a slurry. In a separate vessel Ligand 1 (0.05 mmol, 18.9 mg) was mixed with FeCl$_2$ (0.05 mmol) and WAIF (2.0 ml) was added. The mixture was stirred at room temperature for 1 h before the solvent was removed under vacuum to provide a green powder. To the powder was added toluene (6.25 mL) to form a fine suspension. From the stirred suspension a 2.75 mL aliquot (0.022 mmol of complex) was transferred to the vial containing the toluene slurry of 13% MAO on silica. The resulting mixture was transferred to a Schlenk tube and heated at 80° C. under nitrogen for 15 minutes. On standing, the green solid settled beneath a colourless toluene supernatant. The solvent was removed in vacuo to provide a free-flowing green powder.

Example 6

Polymerisation Using a Supported Catalyst

Into a Schlenk tube was weighed the supported catalyst prepared in Example 5 (25 mg, 0.0055 mmol Fe) and toluene (20 mL) was added. Scavenger was added (10% MAO in toluene, 1.0 mL) and the Schlenk tube was evacuated and re-filled with ethylene. The mixture was then stirred under 1 bar ethylene atmosphere for 1 hour, after which a mass-gain of 3.93 g was recorded corresponding to an activity of 786 gPE/mmol Fe/h/bar. The reaction was quenched by addition of acidified methanol, and the white solid polymer product was isolated by filtration and dried overnight at 40° C. GPC analysis showed Mn=600, Mw=1600, Mw/Mn=2.7, Mpk=600. $^{13}$C NMR analysis of solid product (/1000C): ethyl branches 2.3; butyl branches 0.5

Example 7

Ethylene Polymerisation with a Co Complex of Ligand 1

In a glovebox, Ligand 1 (0.005 mmol) was mixed with CoCl$_2$ (0.005 mmol) in THF (1.0 mL). The mixture was stirred at room temperature for 1 h before the solvent was removed under vacuum. To the residue was added toluene (1.0 mL) and a solution of 10% MAO in toluene (1.0 mL). The resulting solution was stirred under an ethylene supply regulated to 0.6 bar, for a duration of 10 minutes. After this time, a weight-gain of 0.041 g was recorded, corresponding to an activity of 70 g/mmol.h.bar

Example 8

Preparation of "Li and 2"

Ligand 2 was prepared using a similar procedure to that outlined in Example 1 for Ligand 1, using dibenzoylpyridine in place of diacetylpyridine. The ligand was found to be >90% pure by $^1$H NMR and IR analysis.

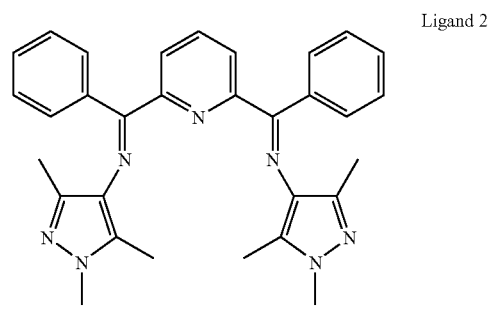

Ligand 2

Example 9

Ethylene Polymerisation using an Fe Complex of Ligand 2

A solution of Ligand 2 (0.5 mL THF solution containing 0.005 mmol of Ligand 2) was added to a solution of FeBr$_2$ (0.5 mL THF solution containing 0.005 mmol FeBr$_2$) to form a dark-green solution. After stirring for 2 hours, the solvent was removed and the residue was redissolved in toluene (1.5 mL). To this was added 10% MAO in toluene (0.5 mL) and the resulting solution was transferred to a Schlenk tube and diluted with toluene (20 mL). The Schlenk tube was evacuated and re-filled with ethylene, then stirred under a 1 bar ethylene atmosphere for 1 hour. A weight-gain of 3.07 g was recorded corresponding to an activity of 614 g/mmol.h.b. The reaction was quenched with acidified methanol and the solid polymer product was isolated by filtration and dried overnight at 40° C. $^{13}$C NMR analysis of solid product (/1000C): ethyl branches 1.6; butyl branches 0.6

Example 10

Ethylene/1-hexene Copolymerisation

A solution of Ligand 2 (0.5 mL THF solution containing 0.005 mmol of Ligand 2) was added to a solution of FeBr$_2$ (0.5 mL THF solution containing 0.005 mmol FeBr$_2$) to form a dark-green solution. After stirring for 2 hours, the solvent was removed and the residue was redissolved in toluene (1.5 mL). To this was added 10% MAO in toluene (0.5 mL) and the resulting solution was transferred to a Schlenk tube and diluted with toluene (20 mL) and 1-hexene (0.5 mL) was added. The Schlenk tube was evacuated and re-filled with ethylene, then stirred under a 1 bar ethylene atmosphere for 1 hour. A weight-gain of 4.30 g was recorded corresponding to an activity of 860 g/mmol.h.b.

The invention claimed is:

1. A polymerisation catalyst comprising (1) a metal complex being a metal M ligated by a monodentate, bidentate, tridentate or tetradentate ligand, wherein at least one of the donor atoms of the ligand is a nitrogen atom substituted by a five-membered heterocyclic substituent joined to the nitrogen atom by a carbon atom, M being selected from Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV] or Nb[V], and (2) an activator compound.

2. The polymerisation catalyst according to claim 1, wherein the metal complex has the Formula (I)

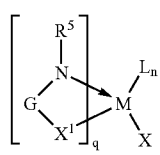

Formula (I)

and wherein the structure $R^5$—N—G—$X^1$ represents a bidentate, tridentate or tetradentate ligand, in which N is a nitrogen joined to G by an imine linkage; G is a bridging group which optionally contains a third or fourth donor atom; $X^1$ is —O or —S if the $X^1$—M bond is covalent, or if the $X^1$—M bond is dative $X^1$ is =S, —$PR^7R^8$, —$PR^8R^9$, =$NR^7$, =$NR^8$, —$NR^7R^8$ or —$NR^8R^9$; $R^5$ is a five-membered heterocyclic substituent joined to the nitrogen atom via a carbon atom; $R^7$ is a five-membered heterocyclic substituent joined to the nitrogen or phosphorus atom via a carbon atom; and $R^8$ and $R^9$ are hydrocarbyl or heterohydrocarbyl, substituted hydrocarbyl or aryl substituent; X represents an atom or group covalently or ionically bonded to the transition metal M; and L is a group datively bound to M, and n is from 0 to 5; q is 1 or 2.

3. The polymerisation catalyst as claimed in claim 2, wherein $X^1$ is =$NR^7$.

4. The polymerisation catalyst as claimed in claim 2 or 3, wherein q is 1, and the ligand is bidentate or tridentate.

5. The polymerisation catalyst as claimed in claim 2, wherein $R^5$ and $R^7$ each independently have the structure

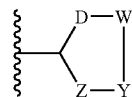

D, W, Y and Z are each independently selected from CR, CRR', N, NR, O, S, PR or PRR' where R and R' are each independently H, $C_1$-$C_{10}$ alkyl, $C_1$-$C_{10}$ heteroalkyl or $C_6$-$C_{20}$ aryl or aralkyl, with the proviso that at least one of D, W, Y and Z is not CR or CRR'.

6. The polymerisation catalyst as claimed in claim 5, wherein the ring is heteroaromatic, with two of D, W, Y and Z being CR, and the other two being independently selected from N, NR, O or S.

7. The polymerisation catalyst as claimed in claim 5, wherein the ring D, W, Y and Z is heteroaromatic, with two of D, W, Y and Z being CR, and the other two being independently selected from N, NR, O or S.

8. The polymerisation catalyst as claimed in claim 2, wherein $R^5$ and $R^7$ have the following structure:

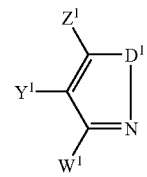

where $D^1$ is NR, O or S, where R is H, $C_1$-$C_6$ alkyl or $C_6$-$C_{20}$ aryl or aralkyl, and two of $W^1$, $Y^1$ and $Z^1$ are independently H, $C_1$-$C_6$ alkyl or $C_6$-$C_{20}$ aryl or aralkyl, while the third is replaced by a direct bond to the nitrogen atom to which $R^5$ or $R^7$ is attached.

9. The polymerisation catalyst as claimed in claim 8, wherein $Y^1$ is replaced by the bond to the nitrogen atom to which $R^5$ or $R^7$ is attached.

10. The polymerisation catalyst as claimed in claim 8, wherein $W^1$ and $Z^1$ are $C_1$-$C_6$ alkyl or $C_6$-$C_{20}$ aryl or aralkyl.

11. The polymerisation catalyst as claimed in claim 8, wherein $D^1$ is NR.

12. The polymerisation catalyst according to claim 1, wherein the metal complex has the Formula (III)

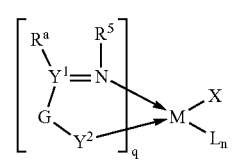

Formula (III)

wherein X represents an atom or group covalently or ionically bonded to the transition metal M; $Y^1$ is C or P(R)$^c$; $Y^2$ is —O($R^7$), —O (in which case the bond from O to M is covalent), C($R^b$)=O, —C($R^b$)=N($R^7$) —P($R^b$)($R^d$)=N ($R^7$) or —P($R^b$)($R^d$)=O; $^5$ and $R^7$ are each independently five-membered heterocyclic substituents joined to the nitrogen atom via a carbon atom; $R^a$, $R^b$, $R^c$, $R^d$ are each independently selected from hydrogen, halogen, hydrocarbyl, substituted hydrocarbyl, heterohydrocarbyl, substituted heterohydrocarbyl or SiR'$_3$ where each R' is independently selected from hydrogen, halogen, hydrocarbyl, and substituted hydrocarbyl, heterohydrocarbyl and substituted heterohydrocarbyl, and any adjacent ones may be joined together to form a ring; G is either a direct bond between $Y^1$ and $Y^2$, or is a bridging group which optionally contains a third atom linked to M when q is 1; L is a group datively bound to M; n is from 0 to 5; and q is 1 or 2 and (2) an activator compound.

13. The polymerisation catalyst as claimed in claim 12, wherein the complex has the formula (IV)

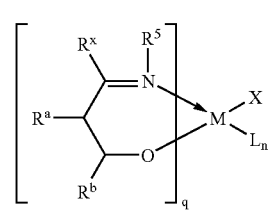

Formula (IV)

wherein X represents an atom or group covalently or ionically bonded to the transition metal M; $R^a$, $R^b$ and $R^x$ are independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; $R^5$ is a five-membered heterocyclic substituent joined to the nitrogen atom via a carbon atom; and L is a group datively bound to M; n is from 0 to 5; and q is 1 or 2.

14. The polymerisation catalyst as claimed in claim 13, wherein the metal M is Ti, Zr, Cr, Ni or Pd.

15. The polymerisation catalyst as claimed in claim 13 or 14, wherein $R^a$ and $R^b$ are joined together to form a phenyl substituent.

16. The polymerisation catalyst as claimed in claim 12, wherein the complex has the Formula (V)

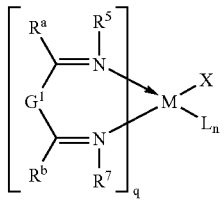

Formula (V)

wherein $R^5$ and $R^7$ are each independently five-membered heterocyclic substituents joined to the nitrogen atom via a carbon atom; $R^a$, and $R^b$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; X represents an atom or group covalently or ionically bonded to the transition metal M; L is a group datively bound to M; n is from 0 to 5; and q is 1 or 2; and $G^1$ is either a direct bond between the two C=N groups, or is a bridging group which optionally contains a third donor atom when q is 1.

17. The polymerisation catalyst as claimed in claim 16, wherein the complex has the Formula (VI):

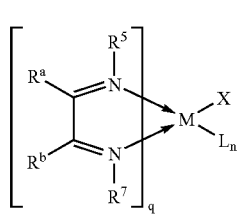

Formula (VI)

wherein X represents an atom or group covalently or ionically bonded to the transition metal M; $R^a$ and $R^b$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; wherein $R^5$ and $R^7$ are each independently five-membered heterocyclic substituents joined to the nitrogen atom via a carbon atom; and L is a group datively bound to M; n is from 0 to 5; and q is 1 or 2.

18. The polymerisation catalyst as claimed in claim 17, wherein M is Ni or Pd.

19. The polymerisation catalyst as claimed in claim 2, wherein the atom or group X is selected from chloride, bromide, hydride, hydrocarbyloxide, formate, acetate, benzoate, methyl, ethyl, propyl, butyl, octyl, decyl, phenyl, benzyl, substituted hydrocarbyl, heterohydrocarbyl, tosylate or triflate.

20. The polymerisation catalyst as claimed in claim 19, wherein the hydrocarbyloxide is methoxide, ethoxide, isopropoxide or phenoxide.

21. The polymerisation catalyst as claimed in claim 19, wherein L is selected from tetrahydrofuran, diethylether, ethanol, butanol, a primary, secondary or tertiary amine, or a phosphine.

22. The polymerisation catalyst as claimed in claim 1, wherein the activator compound is selected from organoaluminium compounds or hydrocarbylboron compounds.

23. The polymerisation catalyst as claimed in claim 22, wherein the activator is an alumoxane.

24. The polymerisation catalyst as claimed in claim 22, wherein the activator is selected from boroxines, trimethylboron, triethylboron, dimethylphenylammoniumtetra(phenyl)borate, trityltetra(phenyl)borate, triphenylboron, dimethylphenylammoniumtetra(pentafluorophenyl)borate, sodium tetrakis[(bis-3,5-trifluoromethyl)phenyl]borate, $H^+(OEt_2)$[(bis-3,5-trifluoromethyl)phenyl]borate, trityltetra(pentafluorophenyl)borate or tris(pentafluorophenyl) boron.

25. The polymerisation catalyst as claimed in claim 1, wherein the activator compound is a salt of a cationic oxidising agent and a non-coordinating compatible anion.

26. A process for polymerising or copolymerising 1—olefins, comprising contacting monomer 1—olefin under polymerisation conditions with the polymerisation catalyst claimed in claim 1.

27. The process as claimed in claim 26, wherein the monomer comprises one or more of ethylene, propylene, 1-butene, 1-pentene, 1-hexene, 4-methylpentene-1, 1-heptene, 1-octene, 1-nonene, 1-decene, 1—undecene, 1-dodecene, 1-tridecene, 1-tetradecene, 1-pentadecene, 1-hexadecene, 1-heptadecene, 1-octadecene, 1-nonadecene, or 1-eicosene.

28. The process as claimed in claim 26, wherein the monomer comprises one or more monomers selected from methyl methacrylate, methyl acrylate, butyl acrylate, acrylonitrile, vinyl acetate, or styrene.

* * * * *